United States Patent [19]

Moore

[11] Plant 4,365

[45] Jan. 16, 1979

[54] MINIATURE ROSE PLANT

[76] Inventor: Ralph S. Moore, 2519 E. Noble Ave., Visalia, Calif. 93277

[21] Appl. No.: 866,807

[22] Filed: Jan. 3, 1978

[51] Int. Cl.[2] ..... A01H 5/00

[52] U.S. Cl. ..... Plt./7

[58] Field of Search ..... Plt./7

*Primary Examiner*—Robert E. Bagwill

[57] ABSTRACT

The subject of this disclosure is a new and distinct variety of miniature rose primarily distinguished by the well shaped orange pink buds and flowers of heavy petal substance produced in abundance, and by the bushy easy to propagate plant.

1 Drawing Figure

The present invention relates to a new and distinct variety of hardy, dwarf, bush type rose plant of the miniature class; the variety being primarily characterized—as to novelty—by coral to orange pink buds and flowers (American Rose Society classifications: Orange blend) which in general color effect are similar to the Floribunda rose Ginger (U.S. Plant Pat. No. 2,293).

The variety is further characterized by:

An abundance of bloom, with flowers usually borne several to the stem in loose cluster (sometimes singly).

Little fragrance.

A plant which is vigorous, of rounded much branched shape with small semi-glossy foliage with pointed leaflets; the buds and flowers being similar in form and size to Starina (miniature — U.S. Plant Pat. No. 2,646).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (U.S. Plant Pat. No. 1,581, expired — Floribunda) as the seed parent and Fire Princess (miniature — U.S. Plant Pat. No. 3,084) as the pollen parent.

Subsequent to origination of the variety I successfully asexually reproduced it at Sequoia Nursery, located at Visalia, Calif., by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: miniature. Variety name: FASHION FLAME.

Flowers borne: singly and several together (3 to 5) on slender wirey stems.

Quantity of bloom: Abundant both outside and in greenhouse.

Bud: Peduncle — medium length; slender but sturdy; erect; medium green, sometimes tinted bronze (outdoors); hairs — usually several. Before calyx breaks; size — small. Form: pointed with several foliaceous appendages and several short hairs on surface of bud; with foliaceous parts extending beyond the tip of the bud equal to one-half of its length. Color — medium green, occasionally tinted with bronze (outdoors). As calyx breaks, color — near orange-red (sometimes whiteish or greenish at base). Opening: opens well in all weather.

Bloom: Size when fully open — small, averaging about 35–40 mm in diameter; 20–25 mm in depth. Petalage — double — averaging about 35 petals, arranged regularly plus sometimes a few small petaloids. Form — high centered at first, becoming more open in the center, with petals rolled loosely outward, and later at maturity open with petals rolled loosely outward and downward. Open flowers may show stamens.

Petals: Fairly thick; satiny on inside and on outside surface. Shape - outside petals, broad lanceolate with almost rounded tip; intermediate — broad lanceolate with slightly acute tip; inside — broad lanceolate with short acute tip.

Color: Newly opened flower from a plant grown in plastic greenhouse (September 1977), Visalia, Calif.:

*Outside petal.*—Outside surface — coral to orange pink, near Azalea Pink 618, on upper ½ to ⅔ of petal blending into lighter area near base. Inside surface — near Azalea Pink 618 (or similar) and blending into lighter area on basal ⅓ of petal.

*Intermediate petal.*—Outside surface — similar to outside petal. Inside surface — similar to outside petal.

*Inner petal.*—Outside surface same as intermediate petal; inside surface — same as intermediate petal.

General color effect; newly opened flowers — coral orange. Three days open — color similar to newly opened flowers. Behavior — opens well in all weather. Flower very long lasting on plant or as cut flower. Spent petals may hang on. Flower longevity (September 1977) — plant in pot 6–10 days or longer. Cut flowers at living room temperature 5–7 days or longer.

Reproductive Organs:

*Stamens.*—Average number, arranged regularly about pistils.

*Filaments.*—Varying length, yellow.

*Anthers.*—Well formed; yellow.

*Pollen.*—Little or none.

*Styles.*—Fairly even; medium length; bunched; near white.

*Stigma.*—Color — near white.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; quite small; leathery; semi-glossy.

*Leaflets.*—Shape: broad, lanceolate; apex acute; base rounded or rounded acute. Margin serrate. Color: medium green; new growth — normal (medium) green (young leaves may be tinted bronze, especially along the serrated edges). Rachis: medium strength; upper side may have several tiny short hairs, grooved; underside — several small thorns with some tiny hairs. Stipules: short — medium width; medium length; narrow points which turn out at more or less than 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; straight, projecting at right angle to stem; color: brown. Prickles: none. Hairs: none.

*Branches.*—Color: light to medium green; new growth often reddish. Thorns: average; long; slender; straight, usually projecting at right angle to stem; color — reddish. Short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, much branched habit, substantially as illustrated and described, characterized by buds and flowers which are coral to orange pink in color, (often deeper colored outdoors), the buds and flowers resembling Starina (miniature — U.S. Plant Pat. No. 2,646) in size and shape but more coral or orange (less red) in color, with petals of heavier substance; said plant being vigorous and compact, easy to propagate from cuttings or by budding, with an abundance of disease resistant small semi-glossy or matt foliage and an abundance of flowers borne singly or several to the stem in loose clusters.

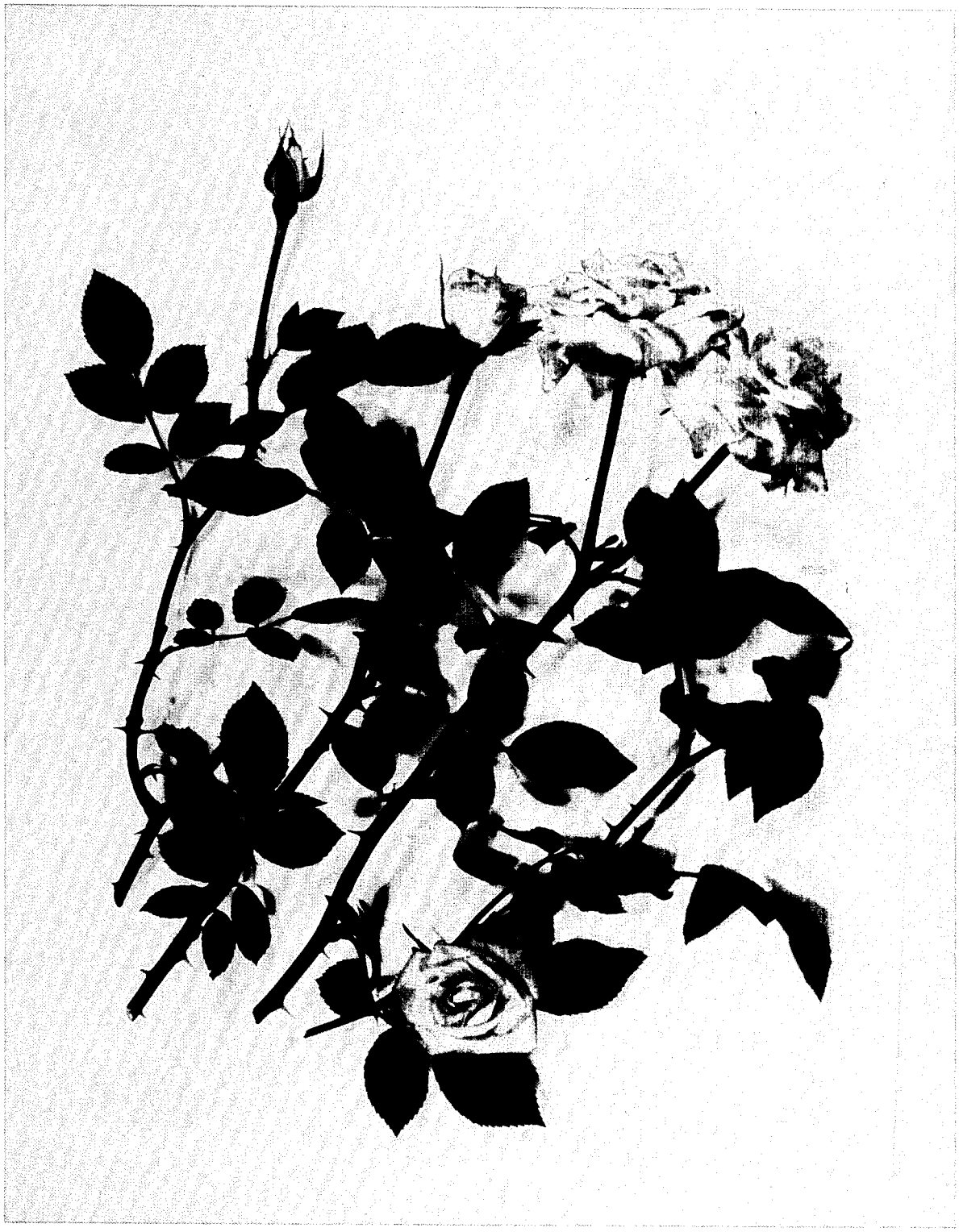

* * * * *